US008880174B1

(12) United States Patent
Abell et al.

(10) Patent No.: US 8,880,174 B1
(45) Date of Patent: Nov. 4, 2014

(54) MEDICAL DIAGNOSTIC AND PREDICTIVE THERAPEUTIC METHOD USING DISCRIMINANT ANALYSIS

(75) Inventors: Thomas Abell, Ridgeland, MS (US); William D. Johnson, Baton Rouge, LA (US); Hani Rashed, Collierville, TN (US)

(73) Assignee: University of Mississippi Medical Center, Jackson, MI (US)

( * ) Notice: Subject to any disclaimer, the term of this patent is extended or adjusted under 35 U.S.C. 154(b) by 708 days.

(21) Appl. No.: 12/844,707

(22) Filed: Jul. 27, 2010

Related U.S. Application Data

(63) Continuation-in-part of application No. 11/773,250, filed on Jul. 3, 2007, now abandoned, which is a continuation of application No. 11/683,158, filed on Mar. 7, 2007, now abandoned.

(60) Provisional application No. 61/228,856, filed on Jul. 27, 2009.

(51) Int. Cl.
*A61N 1/00* (2006.01)

(52) U.S. Cl.
USPC .......................................................... 607/40

(58) Field of Classification Search
USPC .................. 128/897, 898, 905, 906, 920–925
See application file for complete search history.

(56) References Cited

U.S. PATENT DOCUMENTS

| | | | |
|---|---|---|---|
| 6,895,279 B2 | 5/2005 | Loeb et al. | |
| 7,072,794 B2* | 7/2006 | Wittkowski | 702/179 |
| 7,249,145 B1 | 7/2007 | Rock et al. | |
| 8,095,389 B2* | 1/2012 | Dalton et al. | 705/3 |
| 2002/0103522 A1 | 8/2002 | Swoyer et al. | |
| 2007/0167687 A1* | 7/2007 | Bertolero et al. | 600/300 |

OTHER PUBLICATIONS

Office Action for U.S. Appl. No. 11/773,250 dated Jul. 6, 2009.
Office Action for U.S. Appl. No. 11/773,250 dated Jun. 14, 2010.
Abell et al., Glucagon-Evoked Gastric Dysrhythmias in Humans Shown by an Improved Electrogastrographic Technique; Gastroenterology, vol. 88, 1985, pp. 932-940.

(Continued)

*Primary Examiner* — Christopher D Koharski
*Assistant Examiner* — Elizabeth K So
(74) *Attorney, Agent, or Firm* — Stites & Harbison PLLC; Stephen Weyer

(57) ABSTRACT

A diagnostic method and predictor of prognosis from various therapeutic treatments is provided using discriminant analysis statistics. In one form, a patient is identified as having a disease using discriminant analysis when one or more values of a physiological parameter of the patient is closer to that of a previously characterized group of individuals having a disease and the patient is diagnosed as not having the disease, or healthy, if the value of a patient's parameter is closer to that of individuals previously characterized as healthy, or not having the disease. For example, the parameters can be based on the autonomic and/or enteric nervous system. Advantageously, the present method can be readily adapted using conventional linear discriminant analysis statistics to factor more than one parameter between a patient and one or more previously classified groups, to thereby enhance predictability and reliability of the present method. Further, in another form, linear discriminant analysis is used to predict outcomes of various therapeutic treatments of a disease to which a patient is afflicted by comparing the value or values of one or more patient parameter with respective ones in previously characterized individuals having the same affliction which have been treated either successfully or unsuccessfully.

18 Claims, 2 Drawing Sheets

(56) References Cited

OTHER PUBLICATIONS

Abell et al., Gastric electromechanical and neurohormonal function in anorexia nervosa; Gastroenterology, vol. 93, No. 5, Nov. 1987, pp. 958-965.
Abell et al., Electrogastrography. Current assessment and future perspectives.; Dig. Dis. Sci., vol. 33, No. 8, Aug. 1988, pp. 982-992.
Abell et al., Gastric electromechanical function and gastric emptying in diabetic gastroparesis; European Journal of Gastroenterology & Hepatology, vol. 3, 1991, pp. 163-167.
Abell et al., Diabetic gastroparesis is associated with an abnormality in sympathetic innervation; European Journal of Gastroenterology & Hepatology, vol. 6, 1994, pp. 241-247.
Abell et al., Gastric electrical stimulation in intractable symptomatic gastroparesis; Digestion, vol. 66, No. 4, 2002, pp. 204-212.
Abell et al., Gastroparesis and the gastric pacemaker; a revolutionary treatment for an old disease [abstract]; J. Miss. State Med. Assoc., vol. 43, No. 12, Dec. 2002, pp. 369-375.
Abell et al., Gastric electrical stimulation for gastroparesis improves nutritional parameters at short, intermediate, and long-term follow-up [abstract]; J. Parenter. Enteral. Nutr., vol. 27, No. 4, Jul.-Aug. 2003, pp. 277-281.
Abell et al., Gastric electrical stimulation for medically refractory gastroparesis; Gastroenterology, vol. 126, No. 2, Aug. 2003, pp. 421-428.
Abell et al., Nutrition Aspects of Gastroparesis and Therapies for Drug-Refractory Patients; Nutrition in Clinical Practice, vol. 21, Feb. 2006, pp. 23-33.
Abell et al., Looking to the Future; Electrical Stimulation for Obesity [Bariatric Surgery]; The American Journal of the Medical Sciences, vol. 331, No. 4, Apr. 2006, pp. 226-232.
Abidi et al., An energy algorithm improves symptoms in some patients with gastroparesis and treated with gastric electrical stimulation; Neurogastroenterol. Motil., vol. 18, No. 4, Apr. 2006, pp. 334-338.
Ayinala et al., Temporary gastric electrical stimulation with orally or peg-placed electrodes in patients with drug refractory gastroparesis; Gastrointestinal Endoscopy, vol. 61, Mar. 2005, pp. 455-461.
Batista et al., Effects of Temporary Gastric Electrical Stimulation With Endoscopically Placed Electrodes: A Report of 41 Consecutive Patients [abstract]; American Society for Gastrointestinal Endoscopy, Apr. 2004.
Cutts et al., Symptom improvement from prokinetic therapy corresponds to improved quality of life in patients with severe dyspepsia; Dig. Dis. Sci, vol. 41, No. 7, Jul. 1996, pp. 1369-1378.
Cutts et al., Is gastric electrical stimulation superior to standard pharmacologic therapy in improving GI symptoms, healthcare resources, and long-term health care benefits?; Neurogastroenterol. Motil., vol. 17, No. 1, Feb. 2005, pp. 35-43.
Familoni et al., Electrical stimulation at a frequency higher than basal rate in human stomach; Dig. Dis. Sci., vol. 42, No. 5, May 1997, pp. 885-891.
Familoni et al., Efficacy of electrical stimulation at frequencies higher than basal rate in canine stomach; Dig. Dis. Sci., vol. 42, No. 5, May 1997, pp. 892-897.
Familoni et al., Driving gastric electrical activity with electrical stimulation; Ann. Biomed. Eng., vol. 33, No. 3, Mar. 2005, pp. 356-364.
Gaber et al., Improvement in Autonomic Function Following Combined Pancreas-Kidney Transplantation, vol. 23, No. 1, Feb. 1991, pp. 1660-1662.
Gaber et al., Improved Autonomic and Gastric Function in Pancreas-Kidney vs Kidney-Alone Transplantation Contributes to Quality of Life; Transplantation Proceedings, vol. 26, No. 2, Apr. 1994, pp. 515-516.
Hathaway et al., Improvement in Autonomic Function Following Pancreas-Kidney Versus Kidney-Alone Transplantation; Transplantation Proceedings, vol. 25, No. 1, Feb. 1993, pp. 1306-1308.
Hathaway et al., Improvement in Autonomic and Gastric Function Following Pancreas-Kidney Versus Kidney-Alone Transplantation and the Correlations with Quality of Life; Transplantation, vol. 57, No. 6, Mar. 1994, pp. 816-822.
Luo et al., Gastric electrical stimulation improves both GI symptoms and gastric emptying in patients with post-surgical gastroparesis [abstract]. Gastroenterology 1999; 116:S0162.
Luo et al., Gastric Electrical Stimulation Is Associated With Improvement in Pancreatic Exocrine Function in Humans; Pancreas, vol. 29, No. 2, Aug. 2004, pp. e41-e44.
Mahalanobis, P.C., On the Generalized Distance in Statistics, Proceedings of the National Institute of Science of India, vol. 2, No. 1, 1936, pp. 49-55.
Rashed et al., Autonomic Function in Cyclic Vomitin Syndrome and Classic Migraine; Digestive Diseases and Sciences, vol. 44, No. 8, Aug. 1999 Supplement, pp. 74S-78S.
Schmieg et al., In Patients with Disordered Post-Surgical Gastric Emptying, Temporary Gastric Electrical Stimulation (TEMPGES) Quickly Improves Symptoms and Gastric Emptying; 45th Annual Meeting of the Society for Surgery of the Alimentary Tract, Publishing No. 543, May 18, 2004.

\* cited by examiner

MEDICAL DIAGNOSTIC AND PREDICTIVE THERAPEUTIC METHOD USING DISCRIMINANT ANALYSIS

CROSS REFERENCE TO RELATED APPLICATIONS

This is a continuation-in-part of U.S. application Ser. No. 11/773,250 filed Jul. 3, 2007, which was a continuation of U.S. application Ser. No. 11/683,158 filed Mar. 7, 2007, now abandoned; and this claims the benefit of provisional patent Application No. 61/228,856 filed Jul. 27, 2009, all herein incorporated by reference.

FIELD OF THE INVENTION

The present invention relates to a method for diagnosing disease and predicting effective therapeutic treatments and in particular a method for diagnosing medical conditions and predicting outcomes of possible therapeutic treatments using discriminant analysis statistics of physiologic data.

BACKGROUND OF THE INVENTION

Physicians use various pieces of information or data when diagnosing a patient's health condition and when prescribing possible therapeutic treatments if a patient is diagnosed with having a disease or abnormal medical condition. The data a physician uses includes information specific to the patient such as physical characteristics including age, weight, sex, and personal medical and family histories. The personal data also may include information which the doctor gleans from the patient including information which the patient expresses him- or herself as well as physiological attributes and values of parameters which a physician measures. A non-exclusive list of physiological parameters include pulse rate, blood pressure, respiration rate, blood chemistries, EKG, and various imaging such as CT scan, MRI.

Typically, when a physician examines a patient, the physician compares the health or medical data from the patient with historical data. In particular, the physician will compare the patient's data with respective data of both healthy individuals and individuals who previously were diagnosed with a disease or other medical condition. The physician usually will compare values of various parameters of the patient with values of respective parameters in a healthy patient population and a diseased patient population. In the case of diagnosis, diabetes, as an example, one parameter that has been previously determined through many years of observing patients with symptoms of diabetes is a fasting glucose level, with a threshold value of 125. Accordingly, if a patient is found to have a fasting blood glucose level of 125 or higher, a physician is likely to suspect that the patient has diabetes.

In a similar manner to which a physician identifies whether a patient has a diseased condition, a physician may determine whether a patient with a disease or medical condition will respond favourably to a particular therapeutic treatment and thus be a good candidate for that particular treatment. Typically, a physician will compare physiological data of the patient having a disease, with values of respective parameters of previous patients having the same disease, and having undergone various methods for treatment. A physician will likely recommend a treatment for the current patient when previously treated individuals having similar medical data as the patient have been treated successfully using one of the various treatments. Likewise, a physician will likely not recommend a therapeutic treatment for the patient if previous individuals having similar medical data to that of the patient were not treated successfully using that therapeutic treatment.

SUMMARY OF THE INVENTION

The present invention relates to a method and system for diagnosing medical conditions, such as disease, and predicting responses to various therapies for various medical disorders. The method and system incorporates discriminant analysis to statistically identify or classify a patient as having one or more medical conditions. In a similar manner, the present method in one form uses discriminant analysis to determine or predict a response that a patient will have to various therapeutic treatments. Advantageously, the present method uses discriminant analysis (DA), a known statistical analysis tool, to separate, i.e., classify or identify, a patient into one or more classes or categories, e.g., healthy or having one or more medical conditions. Those familiar with statistics will readily understand that DA separates items, e.g., people, events, or things, into one or more categories, often referred to as "groups", by comparing attributes or values of the thing to be classified with respective attributes or values of objects or things in previously classified groups. In DA, an unclassified item, in this case, a patient, is identified as belonging to the group having attributes, e.g., parameter values closer to the items in one group, than to the items in any other group being compared with the item to be classified.

DA applied in the present method compares values of physical, historic, and/or physiological parameters of a patient with respective values from other individuals who have been previously assigned to, or categorized into, various groups. Such individuals include those who had been previously classified in groups such as healthy individuals and those identified as disease afflicted individuals. Using DA, respective values for one or more patient characteristics are compared with respective values of individuals previously classified (i.e., healthy or having one or more diseases or medical conditions). A separate standardized squared distance, or composite score, also referred to in the statistics field as a "linear classifier" for dimensionality reduction (if comparing more than a single parameter) is generated by comparing the data from the patient to the data from the group of healthy individuals and then to the data from the group of diseased afflicted individuals. A patient is classified as belonging to the disease group, i.e., having the disease condition, if the standardized squared distance or composite score based on a comparison of the patient's data with the average (center or centroid) of the disease group's data is less than the standardized squared distance or composite score based on a comparison of the patient's data with the centroid of the healthy group. In other words, if the composite score for the disease group is smaller than the composite score for the healthy group, then the patient's data is closer to the average for the diseased group than to that for the healthy individuals. Accordingly, the smaller difference in compared values, using DA, classifies the patient in the group having values more similar to that of the patient.

The present method can be extended to classify, i.e., identify a possible disease condition, among more than two groups (e.g., healthy and more than one afflicted group). For example, there can be more than one disease afflicted group. In such an instance, DA is applied in the same manner as when comparing values of a patient's parameters to two groups. A composite score or standardized distance is calculated to estimate the gap between the patient's data and the centroid of each classified categorical group of interest. The patient will be assigned the group having the lowest composite score, representing the group whose individuals on average have data values most similar, i.e., closest, to those of the patient.

In one application of the present method a patient having been identified as having a disease, is determined to be a good candidate for a treatment regimen if that patient's composite score, based on successfully treated individuals, is less than his/her composite score based on individuals who were similarly treated but had unsuccessful outcomes.

Advantageously, a historical database for persons whose disease status is known can be used in a discriminant analysis involving multiple physiological parameters to identify a composite scoring system for classifying other persons whose disease status is unknown. Again, interest may be in classifying individuals as healthy or disease afflicted (diagnostic method) or in discriminating successfully unsuccessfully treated disease afflicted individuals (predictive method). As a result, the diagnostic method and predictive method both can use multiple parameters in a single diagnostic and predictive manner to enhance classification accuracy.

The present method can be used for predicting therapeutic treatment for many nutritional and metabolic disorders, including predicting intervention such as transplantation, drugs, or devices. A non-exclusive list includes but is not limited to cyclic vomiting syndrome, diabetic gastroparesis, idiopathic gastroparesis, renal failure, autonomic dysfunction post kidney transplant, hepatic failure, diabetes, catecholamines, hyperemsis gravidarum, liver transplant, drug therapy effects on the autonomic nervous system (ANS) and the enteric nervous system (ENS), pancreas and renal transplantation, implantable devices on ANS and ENS, gastric electrical stimulation therapy, an autonomic and enteric model (ACEM) to predict when to transplant, toxic effects such as radiation or chemotherapy, predictive response to obesity therapy, ACEM for cyclic vomiting syndrome (CVS), ACEM for medical devices, ACEM for diabetes, ACEM for gastroparesis (GP), ACEM for gastrointestinal motility disorders, ACEM for nutritional disorders, ACEM for predicting response to surgical therapies, ACEM for urological and gynecological disorders, ACEM for gastric electrical stimulation response, pediatric feeding disorders, cardiac failure evaluation, cardiac evaluations, Parkinson's disease, etc. When ANS and/or ENS are used to diagnose and/or predict therapeutic treatment outcome, values of various ANS and/or ENS parameters are measured in a patient, and those values are compared to historical data of healthy and/or disease afflicted individuals using the present method which incorporates DA, to diagnose and/or predict the outcome of possible therapeutic treatments.

In its most general sense, the present method uses discriminant analysis to factor a single physiological parameter. Accordingly, the diagnosis and prediction of viable therapies will be based on comparing one or more respective values or ranges of the single parameter of a patient to corresponding value or values of the same parameter of individuals previously classified or characterized into groups, such as healthy or having a diseased condition. Advantageously, the data regarding individuals being healthy or having a diseased condition will be in the form of the mean or average values of all individuals in each group within a historic database classified as one of healthy and disease afflicted individuals. It will be clear to those skilled in statistics that a larger sample size of individuals will produce a better statistical analysis result.

Advantageously, the present method is implemented using a computer in which the patient and historical data of prior individuals are stored in computer memory in an electronic database and a computer processor is used for the statistical calculations.

In the simplest form, the discriminant analysis proceeds by calculating the mean and standard deviation for the single parameter. If one were to consider the example that a patient's fasting plasma glucose level of greater than 125 is an indication that a patient may have diabetes, the parameter to be considered is the value of the fasting plasma glucose, denoted by the variable x. Accordingly, $x_1$, $x_2$, corresponds to the fasting glucose in each of two groups namely, Group 1, individuals previously determined through rigorous diagnosis (e.g., glucose tolerance test) to be afflicted with diabetes, and Group 2, healthy individuals.

Denote the sample means for the two groups as $\bar{x}_1$ and $\bar{x}_2$, respectively, and the standard deviations as $s_1$ and $s_2$, respectively. Let $x_{New}$ represent the fasting plasma glucose level for a new patient whose glucose tolerance test result is unknown. One considers two quantities:

$$D_1^2 = \left(\frac{x_{new} - \bar{x}_1}{s_1}\right)^2 \text{ and } D_2^2 = \left(\frac{x_{new} - \bar{x}_2}{s_2}\right)^2 \quad (I)$$

$D_1^2$ represents a quantity known as the standardized squared distance between $x_{New}$ and the mean for (diabetic Group 1). Similarly, $D_2^2$ represents the standardized squared distance between $x_{New}$ and the mean for (non-diabetic Group 2). Squared distance is used to avoid obtaining negative distances. In accordance with discriminant analysis, one employs the rule: classify the new patient in the group with the smallest squared distance; that i.e., one classifies a new patient whose glucose level is $x_{New}$ in the group with mean "closest to" $x_{New}$. Thus, the new patient will be assigned to Group 1 (diabetic) if $D_1^2 < D_2^2$ and otherwise, the new patient is assigned to Group 2 (non-diabetic).

If $s_1 = s_2 = s$, the decision rule can be restated as assign to Group 1 if $$\left(\frac{x_{new} - \bar{x}_1}{s}\right)^2 < \left(\frac{x_{new} - \bar{x}_2}{s}\right)^2 \quad (II)$$

or, simplifying, assign to Group 1 if $$-2\left(\frac{\bar{x}_1}{s^2}\right)x_{new} + \left(\frac{\bar{x}_1^2}{s^2}\right) < -2\left(\frac{\bar{x}_2}{s^2}\right)x_{new} + \left(\frac{\bar{x}_2^2}{s^2}\right) \quad (III)$$

or, equivalently, assign to Group 1 if (note the change in direction of the inequality)

$$2\left(\frac{\bar{x}_1}{s^2}\right)x_{new} - \left(\frac{\bar{x}_1^2}{s^2}\right) > 2\left(\frac{\bar{x}_2}{s^2}\right)x_{new} - \left(\frac{\bar{x}_2^2}{s^2}\right) \quad (IV)$$

The expression also can be written in the general form $$a_1 x_{New} + b_1 < a_2 x_{New} + b_2 \quad (V)$$

but caution must be exercised in choosing the direction of the inequality.

EXAMPLE

Suppose an investigator, e.g., a physician, finds 20 patients to be diabetic (Group 1) and another 30 patients to be non-diabetic (Group 2) by the glucose tolerance test. The investigator then measures each patient's fasting plasma glucose level and finds the mean and standard deviation to be $\bar{x}_1=145$ and $s_1=12$ mg per deciliter for the diabetic group, with $\bar{x}_2=75$ and $s_2=14$ mg per deciliter for the non-diabetic group. Substituting in the formulation given above, one gets:

$$D_1^2 = \left(\frac{x_{New}-145}{12}\right)^2 \text{ and } \left(\frac{x_{New}-75}{14}\right)^2 \quad (VI)$$

In which $D_1^2$ represents a linear classifier based on a comparison with diabetes afflicted individuals and $D_2^2$ represents a linear classifier based on a comparison with healthy individuals. Using a pooled estimate of standard deviation under the assumption of equal population standard deviations and simplifying, one generates two discriminant expressions:

$$D_1 = -1.9168 x_{New} + 138.9715$$

and $$D_2 = -0.9915 x_{New} + 37.1802 \quad (VII)$$

Now suppose a "new" patient's fasting plasma glucose level is measured and found to be $x_{New}=114$ mg per deciliter without conducting the glucose tolerance test. Substituting 114 into the discriminant equations and find $$D_1 = -1.9168(114) + 138.7715 = -79.7437$$

and $$D_2 = -0.9915(114) + 37.1802 = -75.8508 \quad (VIII)$$

Because $D_1 < D_2$ (i.e., $-79.7437 < -75.8508$), one classifies the patient as diabetic. The discriminant analysis can be extended to use two or more screening variables and the discriminant analysis can be extended to include more than two groups beyond diseased or not diseased groups, which will now be apparent to one with knowledge of conventional statistics. Similarly, discriminant analysis can be used to predict likely successful candidates for one or more treatments based on a historical database which includes individuals having the same disease condition as the patients who have undergone respective different types of successful or unsuccessful treatments. The present invention in one form thereof relates to a diagnostic method for diagnosing a disease condition. The method includes accessing a database comprising medical data from individuals previously classified as healthy individuals and disease afflicted individuals. Respective values are measured for one or more physiological parameters from a patient. Two composite scores are calculated by applying discriminant analysis functions which factor the measured value or values of the patient, respectively, with (1) the data from healthy individuals to calculate a healthy composite score and (2) the data from the disease afflicted individuals to calculate a disease afflicted composite score. The two composite scores are compared and a patient is identified as having a disease when the disease composite score is less than the healthy composite score. In other words, the patient is assigned to the group whose composite score is smaller. If the method is applied to consider a second disease, the patient is assigned to the group whose composite score is the smallest.

In one advantageous form, the medical data from healthy individuals and diseased individuals is in an electronic database comprising the mean or averages of the measured values for the respective parameters. Further, in an alternative embodiment, the applied discriminant analysis functions calculate the composite scores using linear discriminant functions. In one specific embodiment, the parameter or parameters compared include ANS and/or ENS values.

The present invention, in another form thereof, relates to a method for not only diagnosing medical conditions using discriminant analysis of physiologic data but for predicting patient response to possible therapeutic treatment. The method includes accessing a database comprising medical data from individuals previously classified as having a disease. The data includes data from the individuals prior to being subsequently subjected to either successful treatment or unsuccessful treatment. The medical data comprises one or more physiological parameters and respective values from one or more individuals. The information includes identification of whether the treatment was successful. Respective values are measured from one or more physiological parameters from the patient. Two composite scores are calculated by applying discriminant analysis functions which respectively factor the data from the patient with (1) data from individuals subjected to successful treatment to calculate a successful treatment composite score and (2) data from individuals subjected to unsuccessful treatment to calculate an unsuccessful composite score. The two composite scores are compared to one another. A patient is identified as a good candidate to receive the treatment when the successful composite score is less than the unsuccessful composite score. In one advantageous form, the method calculates composite scores based on the mean values of one or more parameters from two or more individuals.

In a further embodiment, the present method can be extended to consider more than one possible treatment. One skilled in the art will readily recognize that in such an instance, composite scores will be generated by factoring the patient's data with data in each treatment group.

DETAILED DESCRIPTION

Figure 1:
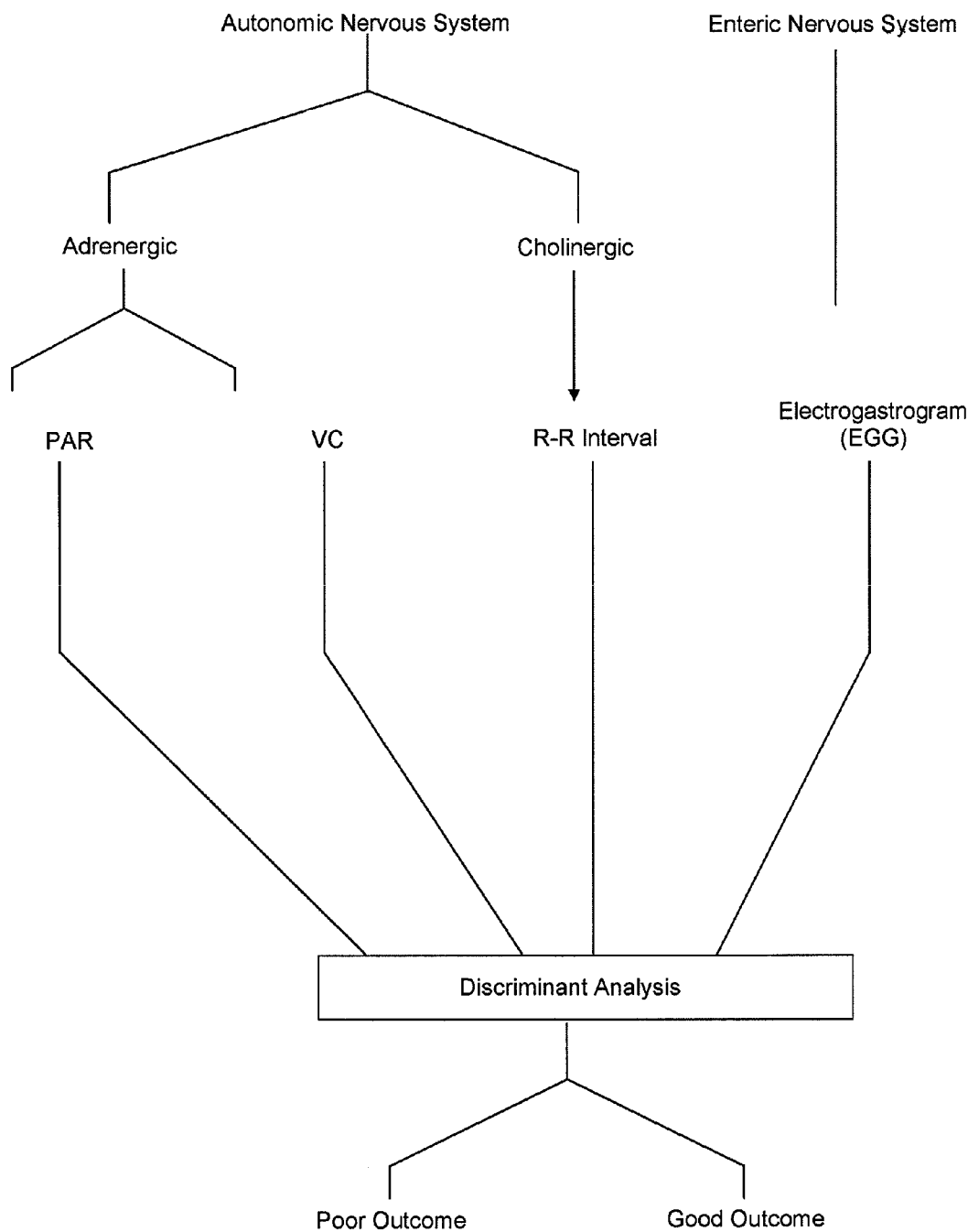
FIG. 1 is a flow chart depicting the use of discriminant analysis in identifying possible outcome of various therapeutic treatments based on measured autonomic nervous system and enteric nervous system values, in accordance with one aspect of the present invention as well as diagnosing conditions where the diagnosis is not immediately obvious.

The present method provides a novel, new approach for diagnosing disease, nutritional, and/or metabolic disorders as well as predicting whether a patient is a good candidate for receiving various treatments. Further, the present method can predict the outcome or results of various therapeutic treatments for diseases, nutritional, and/or metabolic disorders as well as predict a response to other interventions such as but not limited to implantation, drugs, or other devices.

The present method uses discriminant analysis to classify or characterize a patient into a predefined group, such as healthy or afflicted with a medical condition. In the most generic application of the use of discriminant analysis in accordance with the present system and method, the value(s) of at least one identified, measured, calculated, or otherwise determined physiological parameter of a patient is compared with corresponding respective value(s) of that parameter in historical data from individuals previously classified or characterized into various groups. When the present method is used to diagnose a disease condition, the historical data will include both healthy individuals and individuals having one or more identified diseases. Individuals in the historical database will be classified in groups such as healthy or as having one or more disease or medical condition.

It should be noted that with regard to parameters and in particular values of parameters which are indicative of disease, while each parameter potentially carries information relevant to diagnosis and prognosis for each disease, it is often difficult to distill the information for all of the parameters in a format that is useful for meaningful interpretation. Factoring a single parameter when comparing a patient to either healthy or disease afflicted individuals may not necessarily lead to accurate diagnosis and prognosis. Therefore, although the present method may factor a single parameter, accuracy is enhanced when more than a single parameter is considered.

The present method and system accommodates comparing more than a single parameter by using a composite scoring system based on the analytical method known as discriminant analysis. In a preferred method, the discriminant analysis uses measurements of multiple parameters from a sample of prior individuals or patients, i.e., historical data, whose diagnosis (or prognosis) outcome is known and comparing this information with respective data from a present patient, to calculate composite scores based on each identified group in the database. From comparing the composite scores, one can diagnose the disease status of patients whose status is previously unknown. Separate, specific scoring systems are provided, one for diagnosis and one for prognosis, which provide composite scoring algorithms for various disease and nutritional conditions.

In practice, when a patient is suspected as having one of the diseases classified in the historical database, measurements for that patient's parameters are substituted into the present diagnostic algorithm for the suspected disease and a composite numerical score is calculated. The value of the resulting calculation is used to classify the patient's diseased status depending on cut-points established by the algorithm. The algorithm also calculates an estimate of the probability that the classification is correct and thus gives a quantitative estimate of the preponderance of evidence in favor of the prognosis. Thus, if a patient is told that based on his/her assessments the probability is approximately 0.12 that he/she has the suspected disease, then the patient can be pretty confident he/she does not have the disease. On the other hand if a patient is told his/her assessments suggest the probability is approximately 0.93 that he/she has the disease then the patient would want to strongly consider management of his/her condition. Note that even if the estimated probability of disease is 0.55, the patient should be followed very closely in an effort to prevent disease progression.

In one further embodiment, when the patient's status becomes known with certainty, the algorithm is updated to incorporate all available known diagnostic information and enhance diagnostic accuracy for future applications. For example, the historical patient database is updated with the information from the now certain diagnosed patient allowing that updated historical database to be used for future patient diagnosis thus leading to enhanced diagnostic accuracy in future applications. A similar application of the present method pertains for prognosis.

Referring now to the present method in further detail, as previously noted, the present method, in its simplest form can be used to classify patients into one of two groups based on a single physiological parameter. For example, referring to the previous diabetes example based on a single parameter, fasting plasma glucose level, a historical database will include diabetic individuals, Group 1, and non-diabetic individuals, Group 2. The historical database will also include respective fasting plasma glucose levels for individuals in both Groups 1 and 2.

If the investigator hypothesizes that a measurement such as fasting plasma glucose level would be a suitable substitute for the glucose tolerance test as a screening tool for diabetes, one first uses the glucose tolerance test to identify or classify individuals as either having diabetes or not having diabetes. Next, one measures the fasting glucose level of the individuals in both the diabetes group and the healthy group. Based on the fasting glucose values measured, a rule is developed for deciding whether a new patient whose glucose tolerance test result is unknown should be diagnosed (classified) as diabetic or non-diabetic. There are many possibilities for developing such a rule. The present method uses the statistical method known as discriminant analysis. The following is a tutorial introduction to the strategy used in deriving a classification rule based on a linear discriminant function.

Denote the sample means for the two groups as $\bar{x}_1$ and $\bar{x}_2$, respectively, and the standard deviations as $s_1$ and $s_2$, respectively. Let $x_{New}$ represent the fasting plasma glucose level for a new patient whose glucose tolerance test result is unknown. One considers two quantities:

$$D_1^2 = \left(\frac{x_{new} - \bar{x}_1}{s_1}\right)^2 \text{ and } D_2^2 = \left(\frac{x_{new} - \bar{x}_2}{s_2}\right)^2 \qquad (I)$$

$D_1^2$ represents a quantity known as the standardized squared distance between $x_{New}$ and the mean for (diabetic Group 1). Similarly, $D_2^2$ represents the standardized squared distance between $x_{New}$ and the mean for (non-diabetic Group 2). Squared distance is used to avoid obtaining negative distances. In accordance with discriminant analysis, one employs the rule: classify the new patient in the group with the smallest squared distance; that i.e., one classifies a new patient whose glucose level is $x_{New}$ in the group with mean "closest to" $x_{New}$. Thus, the new patient will be assigned to Group 1 (diabetic) if $D_1^2 < D_2^2$ and otherwise, the new patient is assigned to Group 2 (non-diabetic).

If $s_1 = s_2 = s$, the decision rule can be restated as assign to Group 1 if $$\left(\frac{x_{new} - \bar{x}_1}{s}\right)^2 < \left(\frac{x_{new} - \bar{x}_2}{s}\right)^2 \qquad (II)$$

or, simplifying, assign to Group 1 if $$-2\left(\frac{\bar{x}_1}{s^2}\right)x_{new} + \left(\frac{\bar{x}_1^2}{s^2}\right) < -2\left(\frac{\bar{x}_2}{s^2}\right)x_{new} + \left(\frac{\bar{x}_2^2}{s^2}\right) \qquad (III)$$

or, equivalently, assign to Group 1 if (note the change in direction of the inequality)

$$2\left(\frac{\bar{x}_1}{s^2}\right)x_{new} - \left(\frac{\bar{x}_1^2}{s^2}\right) > 2\left(\frac{\bar{x}_2}{s^2}\right)x_{new} - \left(\frac{\bar{x}_2^2}{s^2}\right) \qquad (IV)$$

The expression also can be written in the general form $$a_1 x_{New} + b_1 < a_2 x_{New} + b_2 \qquad (V)$$

but caution must be exercised in choosing the direction of the inequality.

EXAMPLE

Suppose an investigator, e.g., a physician, finds 20 patients to be diabetic (Group 1) and another 30 patients to be non-diabetic (Group 2) by the glucose tolerance test. The investigator then measures each patient's fasting plasma glucose level and finds the mean and standard deviation to be $\bar{x}_1=145$ and $s_1=12$ mg per deciliter for the diabetic group, with $\bar{x}_2=75$ and $s_2=14$ mg per deciliter for the non-diabetic group. Substituting in the formulation given above, one gets:

$$D_1^2 = \left(\frac{x_{New} - 145}{12}\right) \text{ and } \left(\frac{x_{New} - 75}{14}\right)^2 \qquad (VI)$$

In which $D_1^2$ represents a linear classifier based on a comparison with diabetes afflicted individuals and $D_2^2$ represents a linear classifier based on a comparison with healthy individuals. Using a pooled estimate of standard deviation under the assumption of equal population standard deviations and simplifying, one generates two discriminant expressions:

$$D_1 - 1.9168 x_{New} + 138.9715$$

and $$D_2 = -0.9915 x_{New} + 37.1802 \qquad (VII)$$

Now suppose a "new" patient's fasting plasma glucose level is measured and found to be $x_{New}=114$ mg per deciliter without conducting the glucose tolerance test. Substituting 114 into the discriminant equations and find $$D_1 = -1.9168(114) + 138.7715 = -79.7437$$

and $$D_2 = -0.9915(114) + 37.1802 = -75.8508 \qquad (VIII)$$

Because $D_1<D_2$ (i.e., $-79.7437<-75.8508$), one classifies the patient as diabetic.

The present method can be advantageously enhanced by screening two or more variables, to thereby enhance accuracy of diagnosis and prognosis. For example, now consider the situation where an investigator wishes to use two screening variables as a substitute for a gold standard system for classifying patients into one of two (or more) groups such as diseased or not diseased. Denote the screening variables as x and y. As before, one uses the "gold standard" to collect a representative sample of patients from each of the two groups. One then measures x and y for each patient in the two samples and develop a classification rule as a function of the x and y data. Denote the means $\bar{x}_1, \bar{y}_1$ for Group 1 and $\bar{x}_2, \bar{y}_2$ for Group 2 and let $s_{xx}, s_{yy}$, represent the variances for x and y and $s_{xy}$, the covariance for x and y. One arranges these terms in vector-matrix form and notation as follows:

$$\hat{\mu}_1 = \begin{bmatrix} \bar{x}_1 \\ \bar{y}_1 \end{bmatrix}, \hat{\mu}_2 = \begin{bmatrix} \bar{x}_2 \\ \bar{y}_2 \end{bmatrix} \text{ and } \hat{\Sigma} = \begin{bmatrix} s_{xx} & s_{xy} \\ s_{xy} & s_{yy} \end{bmatrix} \qquad (IX)$$

Let $$X_{new} = \begin{bmatrix} x \\ y \end{bmatrix} \qquad (X)$$

represent x and y data for a new patient whose gold standard classification is unknown. A decision rule for classifying the disease status of this new patient is based on distance measures analogous to those used before for a single classification variable. Distance functions can be expressed in vector-matrix expressions as follows:

$$D_1^2 = (X_{new} - \hat{\mu}_1)^T \Sigma^{-1} (X_{new} - \hat{\mu}_1) \text{ and } D_2^2 = (X_{new} - \hat{\mu}_2)^T \Sigma^{-1} (X_{new} - \hat{\mu}_2) \qquad (XI)$$

where $D_1^2$ and $D_2^2$ measure the squared distance between the vector of x and y measurements and the mean vectors $\hat{\mu}_1$ and $\hat{\mu}_2$, respectively. These distance measures can be simplified to discriminant equations of the form:

$$D_1 = a_1 x_{new} + a_2 y_{new} + a_3 \text{ and } D_2 = b_1 x_{new} + b_2 y_{new} + b_3 \qquad (XII)$$

If $D_1<D_2$, one assigns the new patient to Group 1; otherwise one assigns the new patient to Group 2. In applying this rule, one uses a linear combination of the measurements x and y to classify patients whose disease status is unknown. This approach to developing classification rules can be extended to an arbitrary number of classification variables. By using linear combinations of the variables, one is often able to develop discriminant equations with better classification capabilities than that obtained by investigating each variable separately or by simply considering the un-weighted sum of the variables. As a result, the present method leads to more accurate diagnosis and prognosis determination.

Referring to the discriminant analysis statistics in further detail, suppose there are p measurements or variables available for constructing an algorithm for classifying a person into one of g groups when that person's group identity is unknown. Arrange the person's data on a column vector and denote that vector by X as follows:

$$X = \begin{bmatrix} x_1 \\ x_2 \\ \vdots \\ x_p \end{bmatrix}$$

Similarly, arrange the means of the p variables for each of the g groups in a column vector; denote the vector of means for the $j^{th}$ population or group by $\mu_j$ where:

$$\mu_j = \begin{bmatrix} \mu_{j1} \\ \mu_{j2} \\ \vdots \\ \mu_{jp} \end{bmatrix}$$

Let $\Sigma_j$ represent the variance-covariance matrix for the p variables in the $j^{th}$ population where:

$$\Sigma_j = \begin{bmatrix} \sigma_{j11} & \sigma_{j12} & \cdots & \sigma_{j1p} \\ \sigma_{j21} & \sigma_{j22} & \cdots & \sigma_{j2p} \\ \vdots & \vdots & \ddots & \vdots \\ \sigma_{jp1} & \sigma_{jp2} & \cdots & \sigma_{jpp} \end{bmatrix}$$

and in the $j^{th}$ population $\sigma_{j12}$ is the variance of $X_1$, $\sigma_{j12}$ is the covariance between $X_1$ and $X_2$, and so on. The vector of p means for the $j^{th}$ population can be viewed as the center or centroid of the cloud of data for the $j^{th}$ population and the variance-covariance matrix can be viewed as a measure of spread of the data in all directions around the centroid. Suppose the data for a single person represented by X are plotted as a single point in p-dimensional space where as discussed above the person's group identity is unknown. The strategy employed here is to classify that person in the group whose centroid is closest to the single point X.

Mahalanobis distance {Mahalanobis P. C. (1936)}. *On the generalized distance in statistics. Proceedings of the National Institute of Sciences of India*, 2, 49-55, hereinafter incorporated by reference, is a measure of the gap between two points in p-dimensional space where the p variables that define this space may be correlated. Mahalanobis distance is usually defined as a squared measure. Thus, $$\Delta_j^2 = (X-\mu_j)^T \Sigma_j^{-1} (X-\mu_j)$$

where $(X-\mu_j)^T$ is the transpose of $(X-\mu_j)$, $\Sigma_j^{-1}$ is the inverse of $\Sigma_j$ and $\Delta_j^2$ is the square of the Mahalanobis distance from the point X to the centroid of the $j^{th}$ population. Mahalanobis distance can be obtained by finding the positive square root of $\Delta_j^2$ but it is sufficient to work with the squared distance. In applications, the population means, variances and covariances are unknown and must be estimated. To obtain estimates of these parameters, a sample of subjects from each population of interest is required and if each subject's group identity is not known with absolute certainty it should be known with reasonable certainty based on some gold standard classification procedure that often may be impracticable or not readily available. The sample data are used to calculate estimates of the parameters $\mu_j$ and $\Sigma_j$; these estimates are then substituted for their respective parameters in the formula to obtain an algorithm for estimating Mahalanobis distance for the gap between points representing data for one or more subjects not in the original sample whose group identities are unknown, and hence for classifying these subjects according to their probable group identities.

Denote the sample estimates of $\mu_j$ and $\Sigma_j$ by $\hat{\mu}_j$ and $\hat{\Sigma}_j$, respectively. An estimate of the square of Mahalanobis distance from the point X to the centroid of the jth population is:

$$D_j^2 = (X-\hat{\mu}_j)^T \hat{\Sigma}_j^{-1} (X-\hat{\mu}_j)$$

In an application with g groups, there will be one expression for estimating the square of Mahalanobis distance for each group; i.e., for j=1, 2, ..., g. The algorithm for predicting the group identity for a specific person whose data may be plotted as the point X is:

(1) Estimate $D_j^2$ for each group; i.e., for j=1, 2, ..., g.

(2) Substitute X into each expression $D_j^2$ and calculate the squared distance estimate for each group to quantify the gap between X and the centroid of each group.

(3) Find the smallest $D_j^2$ to identify the closest centroid and classify the person as belonging to the corresponding group.

Ordinarily, the distributional clouds of data surrounding the centroids of the g groups will not be clearly separated and these overlapping distributions will lead to classification errors. The goal is to minimize the probability of misclassifying subjects into the groups, but the extent to which a low probability of misclassification is achievable is determined by the amount of overlap in the distributions. Greater separation can sometimes be realized by adding additional discriminatory variables and improving measurement techniques for all the variables. Estimates of misclassification probabilities, or equivalently correct classification probabilities, can be obtained by analyzing two independent sets of samples where the group identity of all subjects is known with reasonable certainty. The first set would be used to estimate $\mu_j$, $\Sigma_j$ and $D_j^2$. Then the expressions $D_j^2$ would be used to classify the subjects in the second set into one of the g mutually exclusive groups. Finally, a tally of the correct and incorrect discriminant expression classifications would be compiled. The proportions of correct and incorrect classifications would provide estimates of the respective probabilities. Note that the same tally could be compiled from data for the first set of samples; however, probability estimates based on this compilation tend to overestimate the true classification probabilities.

The present method can be applied to diagnosing diseases including but not limited to obesity, diabetes mellitus, chronic nausea and vomiting and other GI motility disorders. The present method can also diagnose other organ failure, to include but not limited to: renal failure, hepatic failure, pancreatic failure, cardiac failure and related disorders. Also included are several disorders of neurologic control that may affect the autonomic and enteric nervous systems, including neuro-degenerative disorders such as Parkinsonism, stroke, and congenital neurologic disorders that may have ANS and ENS manifestations. Additional disorders are provided in the examples to follow.

Examples of various parameters which are indicative of or predictive of various disorders and a comparison with the values of individuals not having various afflictions are provided in Table 1 below:

TABLE 1

| predictive of | [parameter 1 /value 1] | [parameter 2 /value 2] | [parameter 3 /value 3] | [parameter 4 /value 4] | [parameter 5 /value 5] |
|---|---|---|---|---|---|
| Healthy Individuals | | | | | |
| Gastric Motility Disorders | % RRI (32 ± 4), Normal Age matched Control (43 ± 10) | VR (1.8 ± 0.1), | VCF (14 ± 2) | PAR (19 ± 60, | % VC (hand) (77 ± 6) |
| Healthy | | Normal (1.77 ± 0.1) | Normal (35 ± 6.5) | Normal (9.9 ± 2) | Normal (43 ± 11) |
| Gastric Motility Disorders (additional parameters) | GET Liquid T50 (74 ± 8) | GET Liquid 60% (52 ± 3) | GET Solid T50 (162 ± 12) | GET Solid 120% (69 ± 4.8) | EGG (3.8 ± 0.2) |
| Healthy | Normal (<60 minutes) | Normal (<50) | Normal (<140 min.) | Normal (<65) | Normal (3 – 3.3) |

TABLE 1-continued

| predictive of | [parameter 1 /value 1] | [parameter 2 /value 2] | [parameter 3 /value 3] | [parameter 4 /value 4] | [parameter 5 /value 5] |
|---|---|---|---|---|---|
| Migraine-like dyspepsia | GET Liquid T50 (93 ± 11) | GET Liquid 60% (59 ± 4) | GET Solid T50 (174 ± 12) | GET Solid 120% (69 ± 4.8) | PAR (9.05 ± 1.15) |
| Healthy | Normal (<60 min.) | normal (<50) | Normal (<140) | Normal (<65) | Normal (>16) |
| Cyclic Vomiting Syndrome | RRI (46.4 ± 4.5) | VR (1.99 ± 0.11) | PAR (8.08 ± 1.3) | SAF (88.3 ± 7.8) | EGG (3.57) |
| Healthy | Normal age matched control (55 ± 3) bpm | Normal (3 ± 0.05) | Normal (11.2 ± 1.63) AU | Normal (99 ± 1.97) | Normal (2.7 – 3.3) cycles/min. |
| Adult Migraine Headaches | RRI (30 ± 3.8) | VR (1.68 v0.1) | PAR (23.2 ± 3.8) | SAF (PAR + % VC) (92 ± 6.6) | EGG (3.7) |
| Healthy | Normal age matched healthy control (52 ± 4) bpm | Normal (1.8 ± 0.1) | Normal (28.7 ± 2) AU | Normal (119 ± 2) | Normal (2.7 – 3.3) CPM |
| Hyperemsis Gravidarum | RRI (29.9 ± 3) | PAR (24.5 ± 5) | % VC (79.4 ± 4.2) | EGG (3.4) | Resting Skin temperature (31.8 ± 0.8) |
| Healthy | Normal age matched pregnant (41 ± 2) | Normal (67.6 ± 11.4) | Normal (87.2 ± 3.6) | Normal (2.7 – 3.3) | Normal (33.8 ± 0.5) 0C |
| Autonomic NS dysfunction post hysterectomy | SAF (91 ± 3.5) | VR (1.6 ± 0.08) | Systolic Blood Pressure change with posture (−4.6 ± 1.18) | Supine Ankle/Brachial Systolic BP ratio (>1.065) | 60 degrees head-up tilt Ankle/Brachial SBP ratio (>1.78) |
| Healthy | Normal age matched Control (117 ± 8.5) | Normal (1.7 ± 0.04) | Normal (8.18 ± 2.2) mm Hg | Normal (<1.065) | Normal (<1.78) |
| hepatic failure | VCF (16.65 ± 2.33) | %VC (66.87 ± 5.9) | PAR (13.5 ± 2.1) | Chatecholamie (2960 ± 500) | Supine Systolic BP (112 ± 2.5) |
| Healthy | Normal age matched healthy Control (35.6 ± 6.55) | Normal (92 ± 1.18) | Normal (32 ± 4.8) | Normal 271 ± 56) | Normal (112 ± 1.7) |
| Diabetes Mellitus | VCF (14.22 ± 1.7) | % VC (53 ± 7.63) | PAR (26.75 ± 7.63) | Serum Catecholamine (226 ± 10) | Supine Systolic BP (135 ± 6.6) |
| Healthy | Normal age matched control (35 ± 6.55) | Normal (92 ± 1.18) | Normal (32 ± 4.8) | Normal (271 ± 56) | Normal (112 ± 1.7) |
| Diabetic gastroparesis | RRI (6.9 ± 1.2) | PAR (13 ± 1.8) | % VC (33.6 ± 7.9) | Resting Skin temperature (31.6 ± 0.9) | Gylcohempglobine (7.6V0.8) |
| Healthy | Normal control (34.6 ± 1.9) bpm | Normal (27.7 ± 2.4) | Normal (81.4 ± 1.5) | Normal (34.4 ± 0.2) | Normal (<6.1) |
| Irritable Bowel Syndrome | % RRI (29.5 ± 2.76) | PAR (51.7 ± 7.77) | % VC (79.7 ± 2.76) | | |
| Healthy | Normal (>30) | Normal (<30) | Normal (>60) | | |

VCF (vago-cholinergic function)
% RRI (percentage of change in heart rate with deep respiration)
Or RRI (change in heart rate with deep respiration)
VR (Valsalva ratio) ratio of maximum vs. minimum heart rate in response to forced respiration.
SAF (Sympathetic Adrenergic Functions which is the sum of % VC and PAR)
% VC (vasoconstriction response in the peripheral circulation in relation to cold stress test)
PAR (postural adjustment ratio response in the peripheral circulation in relation to body posture)
GET (Gastric Emptying Test)

Exemplar physiological parameters and respective values for possible viable treatments of various disease conditions before and after treatment are summarized in Table 2 below:

TABLE 2

| Viable Treatment for | [parameter 1 /value 1] | [parameter 2 /value 2] | [parameter 3 /value 3] | [parameter 4 /value 4] |
|---|---|---|---|---|
| Obesity (post partial gastrectomy) Baseline vs. one year follow-up | EGG (weight losers) (Baseline 2.8 ± 0.13), (weight gainers) (3.5 ± 0.11) | VCF (Baseline Wt. losers) (22 ± 2.3), wt. gainers (26.2 ± 3.4) | SAF (Baseline Wt. losers) (105 ± 5.7), Wt. gainers (83 ± 8.3) | TAS (Baseline Wt. losers) (154.7), Wt. gainers (147.3) |
| diabetes | VCF (Mean 14 +/− 1.7) | % VC (Mean 53 +/− 7.6) | PAR (mean 26 +/− 7) | Catcholamine (mean 226 +/− 10) |
| Gastroparesis in response to GES | Pancreatic polypeptide/On | Area Under Curve/On/ | Serum pancreatic polypeptide | Serum pancreatic polypeptide (post |

TABLE 2-continued

| Viable Treatment for | [parameter 1 /value 1] | [parameter 2 /value 2] | [parameter 3 /value 3] | [parameter 4 /value 4] |
|---|---|---|---|---|
| (On vs. Off) | (208 ± 1290), GES (Off) (280 ± 1907) | (103,178 ± 67,169), Off (84,086 ± 55,649) | (fasting)/On (120 ± 73), Off (127 ± 83) | prandial)/On (1220 ± 745), Off (906 ± 606) |
| Gastroparesis in response to GES (On/Off) additional parameters | (Heart rate variability (low Frequency)/On (4.9 ± 0.46), Off (4.8 ± 0.41) | High frequency, On (4.1 ± 0.3), Off (3.7 ± 0.34) | Low/High ratio On (1.1 ± 0.07), Off (1.4 ± 0.1) | Total Power On (6.1 ± 1.6), Off (5.9 ± 0.39) |
| Gastroparesis in response to GES (baseline vs. follow-up) | EGG (baseline) (3.8 ± 0.2), Follow-up (3.6 ± 0.1) | VCF (22 ± 2.3), Follow-up (26.19 ± 3.4) | SAF (105 ± 5.7), post GET follow-up (83 ± 8.4) | GET Solid 120, baseline (118.7 ± 16), follow-up (89.3 ± 13) |
| Behavioral intervention outcome predictor values (biofeedback training in patients with gatroparesis | RRI (Baseline in non-improved patients post intervention (29 ± 4), (baseline in improved patients (35 ± 5) | VR (non-improved) (1.7 ± 0.1), Improved (1.9 ± 0.18) | % VC (non-improved) (73 ± 8.9), Improved (80 ± 3.2) | GET Liquid T50 (Non-improved) (106 ± 14.9), Improved (58.3 ± 70 |

TAS (Total Autonomic Score)
VCF (vago-cholinergic function)
% RRI (percentage of change in heart rate with deep respiration)
Or RRI (change in heart rate with deep respiration)
VR (Valsalva ratio) ratio of maximum vs. minimum heart rate in response to forced respiration.
SAF (Sympathetic Adrenergic Functions which is the sum of % VC and PAR)
% VC (vasoconstriction response in the peripheral circulation in relation to cold stress test)
PAR (postural adjustment ratio response in the peripheral circulation in relation to body posture)
GET (Gastric Emptying Test)

The present method can be adapted for use with parameters associated with the autonomic nervous system (ANS) which is part of the control system for many of the functions important to human homeostasis including various gastrointestinal, eating and weight control and overall metabolism. Likewise, the present method can be adapted for parameters associated with the enteric nervous system (hereinafter "ENS") which relates to the overall control of the gut. The present method can be adapted for measuring the ANS that can be used to diagnose certain disorders as well as to predict which patients may respond to certain therapies. Likewise, ENS measurements can be added to the overall system to help enhance the diagnosis and prediction of responses to various treatments of the present method and system.

The ANS data and measurement system advantageously includes measurements of adrenergic, cholinergic, and metabolic (hereinafter "ACEM") that can be used via the present algorithm method for diagnosis and predictive purposes. In accordance with the present method and system, once the data is obtained, the data is analyzed first by pattern recognition to add in the associated medical conditions, and then by the present discriminant analysis to predict which patients may respond to certain therapies. Examples of where the ACEM system may be diagnostic include but are not limited to obesity, diabetes mellitus, chronic nausea and vomiting, and other gastrointestinal motility disorders, primary or secondary autonomic disorders, among other medical conditions.

Examples of where the ACEM system may be predictive of therapeutic response include therapies for obesity, diabetes mellitus, gastrointestinal motility disorder, neurological stimulation therapies for any organ system and with central, autonomic or enteric nervous system disorders.

Reference is now made to FIG. 1 which shows a schematic flowchart of how a diagnostic method in accordance with the use of the present discriminant analysis can be used to factor parameters associated with the autonomic nervous system and the enteric nervous system to predict whether a various treatment will have a poor outcome or a good outcome. Although FIG. 1 shows several parameters which are measured and used for discriminant analysis diagnosis, other physical parameters can be measured for diagnosis in accordance with the present method including those referred to in the examples to follow.

The following, Table 3, summarizes various parameters and respective values for use with an ACEM system in accordance with the present discriminant analysis system and method:

TABLE 3

| Viable Treatment for | Parameter | Sensitivity (units) | Specificity (units) | Clinical Diagnostic Value (units) |
|---|---|---|---|---|
| "Normal"/ "Healthy" Control | | | | |
| 1) Behavioral Intervention outcome in patients with chronic gastric motility disorders | 1. GET* Liquid/T50 Liquid/60% Solid/T50 Solid/120% | 61.5 81.8 69.2 92.3 | 85.7 71.4 71.4 50 | 73.6 76.6 70.3 71.15 |
| | 2. AFT** % CHR VR PAR % VCH % VCF | 93.3 80 53.3 86.7 63.6 | 25 33.3 58.3 25 77.8 | 59.2 56.7 55.8 55.9 70.7 |
| 2) EGG can predicts urodynamic dysfunctions in patients with gastroparesis | 1. DM a. 1st. Sens. b. Capacity c. PORV | 86 77 100 | 29 100 36 | 57.8 88.5 68 |

TABLE 3-continued

| Viable Treatment for | Parameter | Sensitivity (units) | Specificity (units) | Clinical Diagnostic Value (units) |
|---|---|---|---|---|
| | 2. Idiop.G | | | |
| | a. 1$^{st}$. Sens. | 90 | 83 | 86.5 |
| | b. Capacity | 91 | 67 | 79 |
| | c. PORV | 60 | 48 | 54 |

*GET(Gastric Emptying Test)
**AFT (Autonomic Function Test)
VCF (vago-cholinergic function)
% RRI (percentage of change in heart rate with deep respiration)
Or RRI (change in heart rate with deep respiration)
VR (Valsalva ratio) ratio of maximum vs. minimum heart rate in response to forced respiration.
SAF (Sympathetic Adrenergic Functions which is the sum of % VC and PAR)
% VC (vasoconstriction response in the peripheral circulation in relation to cold stress test)
PAR (postural adjustment ratio response in the peripheral circulation in relation to body posture)
DM (Diabetes mellitus)
1st. Sens (first sensation)
PORV (post void residual volume)
Idiop. (Idiopathic gastroparesis)

Figure 2:
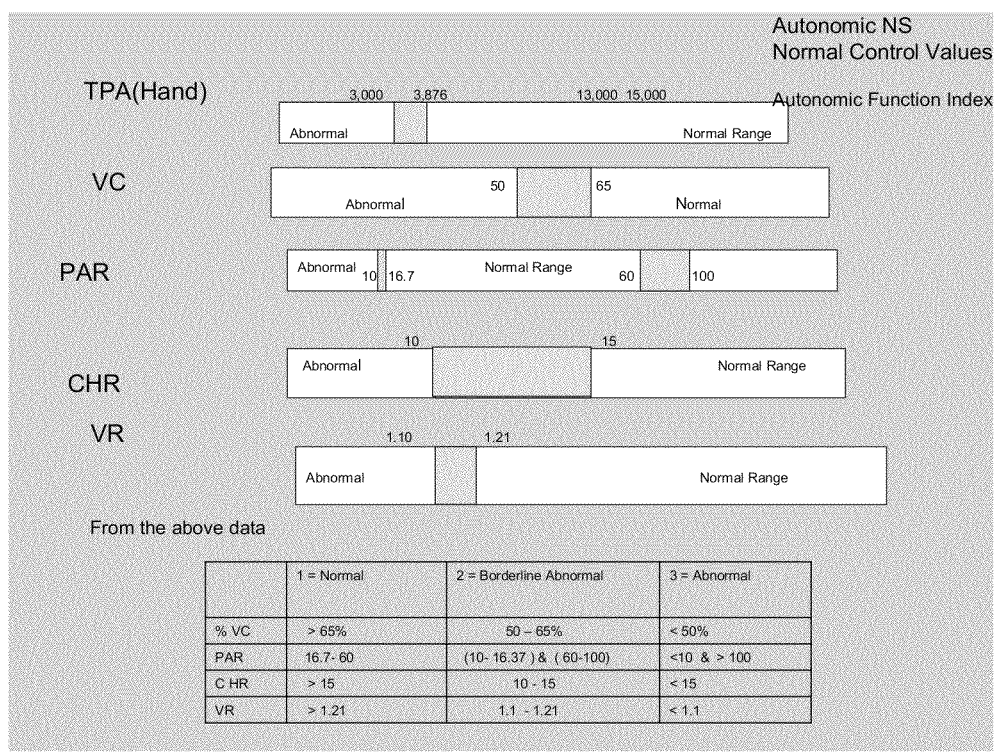
FIG. 2 is a chart showing values for various parameters, in accordance with the present invention.

Referring now to FIG. 2, the top section is a linear representation of the values and how they can be 'graded'. These graded values are summarized in the table at the bottom of FIG. 2.

The following example is provided to enhance understanding of the use of the present method to predict patient outcome.

The 39 gastric restriction patients whose EGG, VC, PAR and RRI values were obtained at the time of surgery (baseline) were followed and their ability or failure to maintain their weight loss (maintainer or gainer) was determined. Using these data with known outcomes as a "rule construction set", the aforementioned discriminant function method was applied to the development of a classification rule for predicting whether a patient should be classified as a future weight gainer or weight loss maintainer following initial weight loss induced by gastric restriction surgery. The result was an index (a linear function) consisting of the sum of a patient's EGG, VC, and RRI (criteria values) where each value in the sum is multiplied by a unique coefficient (weight). The four coefficients were determined from the construction set and remain constant once they are determined. The rule is to substitute a patient's criteria values into the linear function to obtain an index for that patient. The method also determines a classification threshold and the numerical index being above or below the threshold determines whether a patient should be predicted to be a future maintainer or gainer. Ideally, the performance of the derived discriminant rule would be evaluated by applying the prediction rule to an independent sample whose maintainer/gainer status is known for each patient. As is often the case an independent sample was unavailable so the rule was applied to the construction set with the results as shown in Tables 4 and 5, below.

Results: A discriminate model based on baseline measures successfully predicted ultimate weight gain in 8 of 10 (80%) patients who subsequently gained weight and weight loss in 24 of 29 (83%) patients. The same model with data at three months post-operatively predicted weight gain in 9 of 10 (90%) patients and weight loss in 24 of 29 (83%) patients, for a total correct classification rate of 33 of 39 patients (85%) (see Table 4).

All patients had initial weight loss but then were stratified into the two categories: losers and gainers. At last follow-up:
  8 of 10 gainers predicted (80%), and
  26 of 29 losers predicted (90%).

A discriminate model based on baseline measures successfully predicted ultimate weight gain in 8 of 10 (80%) patients who subsequently gained weight and weight loss in 24 of 29 (83%) patients who in subsequently lost weight for a total correct classification rate of 32 of 39 (82%).

Using Quadratic Model from Baseline: Each Patient Classified by ENS/ANS.

The same model with data at 3 months post-operatively predicted weight gain in 9 of 10 (90%) patients and weight loss in 24 of 29 (83%) patients, for a total correct classification rate of 33/39 pts (85%) (see Table 4).

An example of the linear variables is noted in Table 5

CONCLUSION

ENS & ANS measures at baseline predicts long-term response to obesity surgery.

Application of GES to obesity should include prospective monitoring of Enteric and Autonomic Nervous Systems.

TABLE 4

| | Predicted Outcome | | | 3 Month Outcome | | |
|---|---|---|---|---|---|---|
| Time | Baseline | Lose | Total | Predicted | Lose | Total |
| Result | Gain | Lose | Total | Gain | Lose | Total |
| Gain | 8 (80%) | 2 | 10 | 9 (90%) | 1 | 10 |
| Lose | 5 | 24 (83%) | 29 | 5 | 24 (83%) | 29 |

TABLE 5

Linear Discriminant Model

| Gainers | | Losers | |
|---|---|---|---|
| Constant | −72.0 | Constant | −75.0 |
| EGG | 23.6 | EGG | 23.9 |
| PAR | −0.04 | PAR | −0.03 |
| RRI | 0.37 | RRI | 0.34 |
| VC | 0.48 | VC | 0.49 |
| Total Calculated | | Total Calculated | |

The total ananomical scores are $$TAS(Gainers) = -72 + 23.6(Egg) - 0.04(PAR) + 0.37(RRI) + 0.48(VC)$$

$$TAS(Losers) = -75 + 23.9(EGG) - 0.03(PAR) + 0.34(RRI) + 0.49(VC)$$

IF TAS(Gainers) TAS(Losers), we predict the patient will be regain most of their lost weight (Gainers).

IF TAS(Gainers)<TAS(Losers), we predict the patient will be maintain their lost weight (Losers).

Example 1

Patient #685: At baseline weight=411 pounds, EGG=3.9, PAR=40, RRI=22.22, VC=88.7.

$$TAS(Gainers) = -72 + 23.6(3.9) - 0.04(40) + 0.37(22.22) + 0.48(88.7) = 69.80$$

$$TAS(Losers) = -75 + 23.9(3.9) - 0.03(40) + 0.34(22.22) + 0.49(88.7) = 68.03$$

Since 69.80>68.03 we predicted the patient would be a gainer. The patients two year weight was 351 pounds so the patient regained most of their lost weight as predicted.

Example 2

Patient #827: At baseline weight=384 pounds, EGG=3.3, PAR=60.6, RRI=50, VC=81.2

TAS(Gainers)=−72+23.6(3.3)−0.04(60.6)+0.37(50)+0.48(81.2)=51.04

TAS(Losers)=−75+23.9(3.3)−0.03(60.6)+0.34(50)+0.49(81.2)=58.82

Since 51.04<58.82 we predicted the patient would be a loser. The patients four year weight was 176 pounds so the patient maintained most of their lost weight as predicted.

In order to provide additional understanding of the present method, the following non-limiting case examples are provided to enhance understanding but not to limit the scope of the present invention in any way.

Case Example 1

ACEM Correlated with Catecholamines

1. Typical Case

Patient with possible sympathetic nervous system dysfunction.

For example a 35 year old white female who has not only cold intolerance and orthostatic hypotension but also disordered GI function manifesting as dyspepsia.

2. How ACEM can be Performed

This non-invasive technique using autonomic and enteric measures, with a focus on variables such as blood pressure, skin temperature, capillary pulse amplitude as well as specific laboratory measures. (like serum sodium that may be especially sensitive to catecholamine abnormalities)

3. How ACEM can be Analyzed for Clinical Use

A patient can be assessed non-invasively with autonomic and enteric parameters, and determined to be normal or abnormal compared to known normal control values, and then, using the present discriminant algorithmic analysis, can recommend specific therapies.

4. Types of Specific Therapies

Based on this analysis, therapies targeting the sympathetic side of the ANS can be recommended: drug, device or behavioral in nature. See, e.g., "Serum Catecholamines and Dysautonomia In Diabetes and Liver Cirrhosis.

Case Example 2

Hyperemeis Gravidarum (HG)

1. Typical Case 22 year old female patient who has had symptoms of HG for 5 months. She has had to be hospitalized repeatedly and now is receiving total parenteral nutrition (TPN) for nutrients.

2. How ACEM can be Performed

Autonomic and enteric measures, using the complete battery described elsewhere, can be measured safely and non-invasively during pregnancy (PG).

3. How ACEM can be Analyzed for Clinical Use

HG, as shown in our unpublished manuscript data, is manifest as a blunting of normal autonomic function response to PG. However, individual HG patients may be different from each other, and using an algorithmic approach, and compared to normal PG control patients values, the specific abnormalities can be profiled.

4. How ACEM can be Used

Using the results of this analysis, specific therapies can be addressed including drugs, behavior and devices, making sure that the safest method will be used.

Case Example 3

Pre-Liver Transplant Evaluation in Patients with Refractory Findings

1. Typical Case 45 year old male with cirrhosis who is being considered for a liver transplant. However, he has not been able to be controlled from his ANS finding: he runs persistently low systolic blood pressure, his serum sodium is low and he has a number of upper gut dyspeptic symptom's that prevent him from taking oral medications regularly.

2. How ACEM can be Performed

Using the previously described ANS and ENS measures of Case Example 1, e.g., blood pressure, skin temperature, capillary pulse amplitude as well as specific laboratory measures—which needs to be also acknowledged in FIG. 1, the patient's specific and unique physiologic profile can be determined. In addition to the demographic can and laboratory measure, all of the Autonomic and Enteric measures are assessed.

3. How ACEM can be Analyzed for Clinical Use

The ACEM profile can be analyzed via algorithms and compared with both normal controls as well as other patients with liver disease to pinpoint specific abnormalities.

4. How ACEM can be Used

The ACEM data can be used to modulate the patient's autonomic and enteric symptoms and also to consider interventions that may prolong life and improve functioning until a decision about a liver transplant can be made.

Also, many patients are not candidates for liver transplant and the approach described above may help identify which patients are candidates and if they are, when they should (optimally) be transplanted.

Case Example

Drug Therapy Effects On ANS and ENS

1. Typical Case

A 62 year old male is has difficulty controlling his blood pressure and appears to have unexplained drops in blood pressure when he takes small doses of medication.

2. How ACEM can be Performed

ACEM can be performed in this patient using standard parameters as described above in the other cases. Particular attention is paid to blood flow and blood pressure measures. In this case, the patient can be studied before and after medication doses.

3. How ACEM can be Analyzed for Clinical Use

ACEM values can be compared with normal values, using the present method which incorporates linear discriminant analysis to identify techniques to see where the patient's abnormalities are.

4. How ACEM can be Used

In this case, specific drug therapy can be modified to improve patient care, based on the results of this measurement and analysis.

Case Example 5

Pancreas and Renal Transplant Evaluation Patients

1. Typical Case 38 year old male with diabetes mellitus (DM) since age 10, being considered for a pancreas and renal transplant. Patient has renal failure and the symptoms of gastroparesis as well as other DM complications. An evaluation is to determine if the patient is a candidate for a transplant and if so, when it should occur.

2. How ACEM can be Performed

Standard ANS and ENS measures are done, to assess the presence of DM effects on the autonomic and enteric nervous system. The positive effect from the treatment of these complications is known, but each patient is different in the end-organ effects from DM.

3. How ACEM can be Analyzed for Clinical Use

The ANS and ENS effects can be compared with normal values as well as post-transplant follow-up values and all of these are analyzed using discriminant analysis in accordance with the present method.

4. How ACEM can be Used

The resultant measure and analysis can help predict the outcome of the transplants and also can help determine the optimal timing of the transplants.

Case Example 6

Implantable Devices on ANS and ENS

1. Typical Case 56 year old white female who is a possible candidate for an implantable cardio-vascular device. Again, the question of how severe the ANS disorder is and when to implant the device are the ways the ACEM may help.

2. How ACEM can be Performed

Standard ACEM.

3. How ACEM can be Analyzed for Clinical Use

The ACEM measures will help define where the physiologic abnormalities are, and using an algorithmic approach, define if the implantable device will help and if so, when it should be implanted.

4. How ACEM can be Used

The data may also help direct additional pharmacologic therapy that can help and perhaps delay the need for device implantation.

Case Example 7

Gastric Electrical Stimulation Therapy

1. Typical Case

A 43 year old female has symptoms of gastroparesis due to DM and also has some ANS symptoms—especially problems with blood pressure. The patient's doctor is interested in a non-invasive assessment of all of these issues.

2. How ACEM can be Performed

Standard ACEM.

3. How ACEM can be Analyzed for Clinical Use

These measures, especially adrenergic and cholinergic with enteric values can be recorded and compared by an algorithm to assess the degree of abnormality. Also, using the ANS and ENS measures, gastric emptying can be predicted, without having to use a radio-active gastric emptying test.

4. How ACEM can be Used

The resultant values can guide therapy: drug, device or behavioral and can also determine if further analysis is needed, if the abnormalities appear severe.

Case Example 8

ACEM To Model When To Transplant

1. Typical Case 48 year old Hispanic female with liver disease is awaiting a liver transplant.

2. How ACEM can be Performed

ACEM can measure adrenergic and cholinergic function, and enteric function. ACEM can be performed on these types of patients as part of the pre-liver transplant evaluation.

3. How ACEM can be Analyzed for Clinical Use

ACEM can evaluate the patients autonomic and enteric status, especially for adrenergic function when compared with other normal and diseased patients.

4. How ACEM can be used

The ACEM analysis can be used to help time the transplant in terms of when is the most optimal time, for maximum reversibility and minimum risk to the patient.

Case Example 9

Toxic Effects Such as Radiation or Chemotherapy

1. Typical Case 68 year old female with breast cancer has not been able to tolerate radiation and/or chemotherapy, although the reasons are not clear.

2. How ACEM can be Performed

Standard ACEM.

3. How ACEM can be Analyzed for Clinical Use

The ACEM findings can be compared with normal controls and compared by discriminant analysis as well.

4. How ACEM can be Used

ACEM analysis may reveal the abnormalities which can then be targeted to try to prevent the toxic effects and/or treat the effects more effectively.

Case Example 10

Predictive Response to Obesity Therapy

1. Typical Case 36 year old female has a BMI of 37 and is troubled by several complications of her morbid obesity.

2. How ACEM can be Performed

Using standardized adrenergic and cholinergic measures along with enteric measurements ACEM can be preformed at baseline.

3. How ACEM can be Analyzed for Clinical Use

The ACEM measures can be compared by discriminant analysis to predict classify the patient as someone likely to benefit or not from specific therapies, such as a restrictive operation.

4. How ACEM can be Used

The ACEM results can be used to predict whether or not specific therapies, such as a restrictive operation, should be preformed or not.

Case Example 11

ACEM for Cyclic Vomiting Syndrome (CVS)

1. Typical case 21 year old male with recurrent episodes of vomiting meeting the criteria for Cyclic Vomiting Syndrome.

2. How ACEM can be Performed

Adrenergic, cholinergic, and enteric function can be measured.

3. How ACEM can be Analyzed for Clinical Use

The ACEM measures can be compared with known values for CVS.

4. How ACEM can be Used

This patients CVS therapy can be tailored depending on the results of the testing.

Case Example 12

ACEM for Medical Devices

1. Typical Case 29 year old male with multiple medical problems is being considered for two medical devices, both of which might affect the autonomic or enteric nervous system.

2. How ACEM can be performed

Standard ACEM, pre-device placements.

3. How ACEM can be analyzed for clinical use

ACEM results can be compared with known normal values and those with for patients who have undergone devices successfully.

4. How ACEM can be Used

The ACEM results can help predict if the results will be successful.

Case Example 13

ACEM for Diabetes Mellitus (DM) and Gastroparesis (GP)

1. Typical Case 40 year old African American female with long standing DM and GP.

However, it is not clear with the DM has caused the GP symptoms.

2. How ACEM can be Performed

Standard ACEM.

3. How ACEM can be Analyzed for Clinical Use

Compare with known values and those of DM GP.

4. How ACEM can be Used

The analysis shows if the patient's symptoms are consistent with diabetes mellitus (DM) and subsequent gastroparesis (GP) c/w DM GP or not and thus may affect therapies. For example, once corrected diagnosis is made, more precise therapies can be prescribed.

Case Example 14

ACEM for Gastrointestinal Motility Disorders

1. Typical Case 37 year old female with symptoms of GI motility disorders.

2. How ACEM can be Performed

Standard ACEM.

3. How ACEM can be Analyzed for Clinical Use

ACEM results can be compared with the known normal values as well as for other GI motor disorders.

4. How ACEM can be Used

Analysis of ACEM can help confirm a diagnosis of GI motor disorders and also help guide therapy.

Case Example 15

ACEM for Nutritional Disorders

1. Typical Case

A 48 year old female is unable to gain weight. The patient also has some autonomic symptoms such as feeling faint when standing up. Intermittent nausea also bothers the patient.

2. How ACEM can be Performed

Standard ACEM.

3. How ACEM can be Analyzed for Clinical Use

Comparing with normal values to determine where the patients abnormalities lie.

4. How ACEM can be Used

Once the abnormality is identified specific therapies can be directed.

Case Example 16

ACEM for Predicting Response to Surgical Therapies

1. Typical Case 38 year old male who is being considered for innovative surgical therapy. However, he has a history of vague cardio-pulmonary symptoms that have not been able to be clearly delineated despite numerous attempts.

2. How ACEM can be Performed

Standard ACEM.

3. How ACEM can be Analyzed for Clinical Use

The ACEM data is examined for possible autonomic and/or enteric dysfunction which may explain some of the unclear symptoms.

4. How ACEM can be Used

In this case the ACEM analysis may show what specific areas of physiology need to be addressed for the surgery to be effective.

Case Example 17

ACEM for Urological and Gynecological Disorders

1. Typical Case

A 52 year old female has both GI and gynecology symptoms as well as urologic abnormalities. This is a group known to have both autonomic and enteric abnormalities.

2. How ACEM can be Performed

Standard ACEM.

3. How ACEM can be Analyzed for Clinical Use

ACEM results can be compared with normal age and sex matched controls.

4. How ACEM can be Used

Specific abnormalities can be identified which may then impact care: either by mitigating standard therapy or by adding new therapies to help adjust of the autonomic and/or enteric abnormalities.

Case Example 18

ACEM for Gastric Electrical Stimulation Response

1. Typical Case 43 year old female with GP symptoms and possible consideration for GES.

2. How ACEM can be Performed

Standard ACEM.

3. How ACEM can be Analyzed for Clinical Use

Since the ACEM response to GES is known the patient's values can be compared with known values for patients who successfully underwent GES.

4. How ACEM can be Used

The patient may be able to receive predicate values for how likely the GES device (which is not without risk and expense) will be successful.

Case Example 19

Pediatric Feeding Disorders

1. Typical Case

A premature infant who was in the NICU for some time, continues to suffer from difficulty feeding, keeping the patient in the hospital.

2. How ACEM can be Performed

A miniaturized version of ACEM equipment is used.

3. How ACEM can be Analyzed for Clinical Use

The values can be compared with standard values for infants.

4. How ACEM can be Used

The finding on ANS and ENS can help define what may be needed to improve feeding and then later discharge the patient with appropriate follow up.

Case Example 20

Cardiac Failure Evaluation

1. Typical Case 52 year old male with cardiac failure. Patient is undergoing evaluation for a heart transplant but also has significant autonomic and enteric symptoms.

2. How ACEM can be Performed

Standard ACEM.

3. How ACEM can be Analyzed for Clinical Use

Results can be compared with those from other organ failure patients.

4. How ACEM can be Used

Results can help predict both timing of transplant as well as how some of the unpleasant symptoms the patent is having might be able to be ameliorated.

Case Example 21

Syncope and Related Cardiac Evaluations

1. Typical Case

A 32 year old female has a recurrent syncope of unclear etiology.

2. How ACEM can be Performed

Standard ACEM.

3. How ACEM can be Analyzed for Clinical Use

The results of the present inventors' work have shown specific patterns with ACEM for syncope. This data will be used to compare and stratify patients.

4. How ACEM can be Used

Once abnormalities can be identified, therapy can be directed more precisely.

Although the invention has been described above in relation to preferred embodiments thereof, it will be understood by those skilled in the art that variations and modifications can be affected in these preferred embodiments without departing from the scope and spirit of the invention.

The invention claimed is:

1. A diagnostic method comprising:
   accessing a database comprising medical data from individuals previously classified as healthy individuals and disease afflicted individuals;
   measuring respective values for one or more physiological parameters from a patient;
   calculating two composite scores by applying discriminant analysis functions which, respectively, factor measured values from the patient with (a) the data from healthy individuals to calculate a healthy composite score and (b) the data from disease afflicted individuals to calculate a disease composite score;
   comparing the two composite scores; and
   identifying a patient as having a disease when the disease composite score is less than the healthy composite score.

2. The method of claim 1, wherein the medical data from healthy individuals and diseased individuals comprises averages of measured values for the respective parameters.

3. The method of claim 1, wherein the applied discriminant analysis functions for calculating the composite scores comprise linear discriminant functions.

4. The method of claim 3, wherein the healthy individuals are assigned to Group 2 and the disease afflicted are assigned to Group 1, and wherein the linear discriminant functions for calculating composite scores based on two parameters comprises:

$$D_1^2 = (X_{new} - \hat{\mu}_1)^T \hat{\Sigma}^{-1} (X_{new} - \hat{\mu}_1)$$

and $$D_2^2 = (X_{new} - \hat{\mu}_2)^T \hat{\Sigma}^{-1} (X_{new} - \hat{\mu}_2)$$

where $$X_{new} = \begin{bmatrix} x \\ y \end{bmatrix}, \hat{\mu}_1 = \begin{bmatrix} \bar{x}_1 \\ \bar{y}_1 \end{bmatrix}, \hat{\mu}_2 = \begin{bmatrix} \bar{x}_2 \\ \bar{y}_2 \end{bmatrix} \text{ and } \hat{\Sigma} = \begin{bmatrix} s_{xx} & s_{xy} \\ s_{xy} & s_{yy} \end{bmatrix}$$

x=value of a first parameter,
y=value of a second parameter,
wherein, if $D_1^2 > D_2^2$ the patient is identified as belonging to Group 1 as having the disease and if not, the patient is identified as belonging to Group 2 as not having the disease.

5. The method of claim 3, wherein the linear discriminant functions for calculating composite scores based on more than two parameters comprises:

$$D_1^2 = (X_{new} - \hat{\mu}_1)^T \hat{\Sigma}^{-1} (X_{new} - \hat{\mu}_1)$$

and $$D_2^2 = (X_{new} - \hat{\mu}_2)^T \hat{\Sigma}^{-1} (X_{new} - \hat{\mu}_2)$$

where $$X_{new} = \begin{bmatrix} x_1 \\ x_2 \\ \ldots \\ x_p \end{bmatrix}, \hat{\mu}_1 = \begin{bmatrix} \bar{x}_{11} \\ \bar{x}_{12} \\ \ldots \\ \bar{x}_{1p} \end{bmatrix}, \hat{\mu}_2 = \begin{bmatrix} \bar{x}_{21} \\ \bar{x}_{22} \\ \ldots \\ \bar{x}_2 \end{bmatrix}$$

$x_1$=value of a first parameter,
$x_2$=value of a second parameter
$x_p$=value of a $p^{th}$ parameter.

6. The method of claim 1, wherein the composite scores are based on one or more mean values of one or more parameters from two or more individuals.

7. A method of claim 1, wherein the one or more parameters comprise autonomic nervous system or enteric nervous system parameters.

8. A method for predicting patient response to possible therapeutic treatment, said method comprising:
accessing a database comprising medical data from individuals previously classified as having a disease, the medical data including data prior to being subsequently subjected to either a treatment which was successful or unsuccessful as well as identification of whether the treatment was successful and/or data from the individuals after treatment, said medical data comprising one or more physiological parameters and respective values from one or more individuals;

measuring respective values for one or more physiological parameters from a patient having the same disease as the individuals in the database;

calculating two composite scores by applying discriminant analysis functions which, respectively, factor the values measured from the patient with (a) the data from the individuals subjected to successful treatment to generate a successful composite score and (b) the data from the individuals subjected to unsuccessful treatment to generate an unsuccessful composite score;

comparing the two composite scores; and identifying a patient as a good candidate to receive the treatment of the individuals in the database when the successful composite score is less than the unsuccessful composite score.

9. The method of claim 8, wherein the composite scores are based on one or more mean values of one or more parameters from two or more individuals.

10. The method of claim 8, wherein the medical data comprises averages of the measured values for the respective parameters.

11. The method of claim 8, wherein the applied discriminant analysis functions for calculating the composite scores comprise linear discriminant functions.

12. The method of claim 11, wherein the individuals successfully treated are assigned to Group 1, and the individuals unsuccessfully treated are assigned to Group 2, and wherein the linear discriminant functions for calculating the composite scores based on two parameters comprises:

$$D_1^2 = (X_{new} - \hat{\mu}_1)^T \hat{\Sigma}^{-1} (X_{new} - \hat{\mu}_1) \text{ and}$$

$$D_2^2 = (X_{new} - \hat{\mu}_2)^T \hat{\Sigma}^{-1} (X_{new} - \hat{\mu}_2)$$

where $$X_{new} = \begin{bmatrix} x \\ y \end{bmatrix}, \hat{\mu}_1 = \begin{bmatrix} \overline{x}_1 \\ \overline{y}_1 \end{bmatrix}, \hat{\mu}_2 = \begin{bmatrix} \overline{x}_2 \\ \overline{y}_2 \end{bmatrix} \text{ and } \hat{\Sigma} = \begin{bmatrix} s_{xx} & s_{xy} \\ s_{xy} & s_{yy} \end{bmatrix}$$

x=value of a first parameter,
y=value of a second parameter,
wherein, if $D_2^2 < D_1^2$ the patient is identified as belonging to Group 1 as being a good candidate for treatment and if not, the patient is identified as belonging to Group 2 as being a poor candidate for treatment.

13. The method of claim 11, wherein the linear discriminant functions for calculating composite scores based on more than two parameters comprises:

$$D_1^2 = (X_{new} - \hat{\mu}_1)^T \hat{\Sigma}^{-1} (X_{new} - \hat{\mu}_1)$$

and $$D_2^2 = (X_{new} - \hat{\mu}_2)^T \hat{\Sigma}^{-1} (X_{new} - \hat{\mu}_2)$$

where $$X_{new} = \begin{bmatrix} x_1 \\ x_2 \\ \ldots \\ x_p \end{bmatrix}, \hat{\mu}_1 = \begin{bmatrix} \overline{x}_{11} \\ \overline{x}_{12} \\ \ldots \\ \overline{x}_{1p} \end{bmatrix}, \hat{\mu}_2 = \begin{bmatrix} \overline{x}_{21} \\ \overline{x}_{22} \\ \ldots \\ \overline{x}2 \end{bmatrix}$$

$x_1$=value of a first parameter,
$x_2$=value of a second parameter
$x_p$=value of a $p^{th}$ parameter.

14. A diagnostic method comprising:

accessing an electronic database comprising medical data from individuals previously classified as healthy individuals and disease afflicted individuals;

calculating two composite scores by applying discriminant analysis functions which, respectively, factor values from a patient with (a) of the data from healthy individuals to calculate a healthy composite score and (b) the data from disease afflicted individuals to calculate an disease composite score;

comparing the two composite scores; and identifying a patient as having a disease when the disease composite score is less than the healthy composite score.

15. The method of claim 14, wherein the medical data from healthy individuals and diseased individuals comprises averages of measured values for the respective parameters.

16. The method of claim 14, wherein the one or more parameters comprise autonomic nervous system and/or enteric nervous system parameters.

17. A method for predicting patient response to possible therapeutic treatment, said method comprising:

accessing an electronic database comprising medical data from individuals previously classified as having a disease the same as a disease afflicting a patient, the medical data including data prior to being subsequently subjected to either successful treatment or unsuccessful treatment as well as identification of whether the treatment was successful and/or data from the individuals after treatment, said medical data comprising one or more physiological parameters and respective values from one or more individuals;

calculating two composite scores by applying discriminant analysis functions which, respectively, factor one or more values of the one or more physiological parameters from the patient with (a) respective values of parameters from the individuals classified as being subjected to successful treatment to generate a successful composite score, and (b) respective values of parameters from the individuals subjected to unsuccessful treatment to generate an unsuccessful composite score;

comparing the two composite scores; and identifying a patient as a good candidate to receive the treatment if the successful treatment composite score is less than the unsuccessful treatment composite score.

18. The method of claim 17, wherein the one or more parameters comprise autonomic nervous system and/or enteric nervous system parameters.

* * * * *